United States Patent [19]

Milby, Jr. et al.

[11] Patent Number: 5,527,303
[45] Date of Patent: Jun. 18, 1996

[54] ABSORBENT ARTICLE WITH EXPANDABLE BACKSHEET

[75] Inventors: John T. Milby, Jr., Harrison; David M. Sageser, Cincinnati, both of Ohio

[73] Assignee: The Procter & Gamble Company, Cincinnati, Ohio

[21] Appl. No.: 375,864

[22] Filed: Jan. 20, 1995

[51] Int. Cl.⁶ ..................................... A61F 13/15
[52] U.S. Cl. ........................ 604/385.1; 604/364
[58] Field of Search ..................... 604/364, 365, 604/368, 385.1, 385.2, 386, 387

[56] References Cited

U.S. PATENT DOCUMENTS

| | | | |
|---|---|---|---|
| 3,776,233 | 12/1973 | Schaar | 128/287 |
| 4,781,711 | 11/1988 | Houghton et al. | |
| 4,787,896 | 11/1988 | Houghton et al. | 604/385.1 |
| 4,790,839 | 12/1988 | Ahr | 604/367 |

Primary Examiner—David H. Willse
Assistant Examiner—Ki Yong O
Attorney, Agent, or Firm—Kevin C. Johnson; Steven W. Miller; E. Kelly Linman

[57] ABSTRACT

The present invention provides a disposable absorbent article such as an incontinent pad that is both comfortable and suitable for absorbing and containing large volumes of bodily liquids without leakage. Such an absorbent article includes a liquid pervious topsheet, a liquid impervious backsheet joined to the topsheet, and an absorbent core positioned between the topsheet and the backsheet. The absorbent core includes a material which expands when wetted. The backsheet includes at least one pleat which is tacked with a liquid soluble adhesive such that when the liquid soluble adhesive is wetted the adhesive dissolves allowing the pleat to expand as the absorbent core expands. The pleats may extend in any direction, but preferably extend either substantially parallel to the longitudinal axis of the article or substantially parallel to the transverse axis of the absorbent article.

9 Claims, 2 Drawing Sheets

ABSORBENT ARTICLE WITH EXPANDABLE BACKSHEET

FIELD OF INVENTION

The present invention relates to absorbent articles such as diapers, incontinent briefs, incontinent pads, diaper holders, training pants, sanitary napkins, pantiliners, and the like and, more particularly, to absorbent articles having an expandable backsheet.

BACKGROUND OF THE INVENTION

Infants and other incontinent individuals wear absorbent articles such as incontinent pads and diapers to receive and contain urine and other body exudates. Absorbent articles function both to contain discharged materials and to isolate these materials from the body of the wearer and from the wearer's garments and bed clothing. Disposable absorbent articles having many different basic designs are known to the art.

There is a growing awareness of the lack of satisfactory products designed for mobile persons with incontinent infirmities. While sanitary napkins, pantiliners, disposable briefs and diapers are available for the mobile incontinent person, such products are not satisfactory from either a comfort or a protection standpoint. Catamenial products such as pantiliners and sanitary napkins are very comfortable to use. However, these products fail to achieve a satisfactory level of containment for high void levels of urine. While diapers and briefs meet the containment needs of the incontinent person, these products lack the comfort and discreteness available from sanitary napkins and pantiliners.

Thus, it is desirable to provide an absorbent article such as an incontinent pad that is comfortable and discrete, yet provides superior protection and containment. In order to achieve the goal of providing such an absorbent article, it is necessary that the absorbent article be capable of rapidly accepting and containing a large volume of liquid within a small surface area; rapidly distributing the liquid efficiently throughout the product; conforming to the body of the wearer; maintaining good body contact (i.e., the maintenance of the article in close proximity to and in conformity with the body of the wearer); and maintaining its integrity even when wetted so as to be effective to accept and contain a subsequent discharge or gush of liquid and to prevent rewet (i.e., recontact of liquids contained in the article with the skin of the wearer due to forces that squeeze the liquid out of the article).

A method for increasing the absorbency of absorbent articles is to provide them with absorbent gelling materials. Absorbent gelling materials are materials which are capable of absorbing large quantities of liquids and which are further capable of retaining such absorbed liquids under moderate pressures. The absorption characteristics of absorbers gelling materials make such materials especially useful for incorporation into absorbent articles such as incontinent pads. Because absorbent gelling material swells and expands upon being wetted, an absorbent core containing absorbent gelling material will also expand when wetted. Because the overwrap is generally firmly affixed around the absorbent article, the only space available for expansion of the absorbent core is within the interior of the absorbent article. Therefore, there is a need to identify absorbent articles having absorbent cores containing absorbent gelling material wherein the overwrap can expand to accommodate the expansion of the absorbent core. Accordingly, it would be advantageous to provide absorbent articles with an expansion means allowing the overwrap to expand as the absorbent core expands.

Therefore, it is an object of the present invention to provide an absorbent article having an overwrap and a releasing means so that when the absorbent core containing absorbent gelling material expands when wetted, the overwrap will expand as the absorbent gelling material expands.

The above and other objectives of the present invention will be more readily apparent when considered in reference to the following description and when taken in conjunction with the accompanying drawings.

SUMMARY OF THE INVENTION

The present invention provides a disposable absorbent article such as an incontinent pad that is both comfortable and suitable for absorbing and containing large volumes of bodily liquids without leakage. Such an absorbent article comprises a liquid pervious topsheet, a liquid impervious backsheet joined to the topsheet, and an absorbent core positioned between the topsheet and the backsheet. The absorbent core includes a material which expands when wetted. The backsheet includes at least one pleat which is tacked with a water soluble adhesive such that when the water soluble adhesive is wetted the adhesive dissolves allowing the pleat to expand as the absorbent core expands. The pleats may extend in any direction but preferably extends either substantially parallel to the longitudinal axis of the article or substantially parallel to the transverse axis of the absorbent article.

BRIEF DESCRIPTION OF THE DRAWINGS

While the specification concludes with claims particularly pointing out and distinctly claiming the subject matter which is regarded as forming the present invention, it is believed that the invention will be better understood from the following description which is taken in conjunction with the accompanying drawings in which like designations are used to designate substantially identical elements and in which:

DETAILED DESCRIPTION OF THE INVENTION

As used herein, the term "absorbent article" refers to devices which absorb and contain body exudates, and, more specifically, refers to devices which are placed against or in proximity to the body of the wearer to absorb and contain the various exudates discharged from the body. The term "disposable" is used herein to describe absorbent articles which are not intended to be laundered or otherwise restored or reused as an absorbent article (i.e., they are intended to be discarded after a single use and, preferably, to be recycled, composted or otherwise disposed of in an environmentally compatible manner). A preferred embodiment of an absorbent article of the present invention is the incontinent pad 20, shown in FIG. 1 and in cross-sectional view in FIG. 2. As used herein, the term "incontinent pad" refers to an absorbent article generally worn by incontinent persons by adhesively attaching the pad directly to the crotch region of the wearer's undergarment. It should be understood, however, that the present invention is also applicable to other absorbent articles such as incontinent briefs, diapers, diaper holders and liners, sanitary napkins, pantiliners, training pants, and the like.

Figure 1:
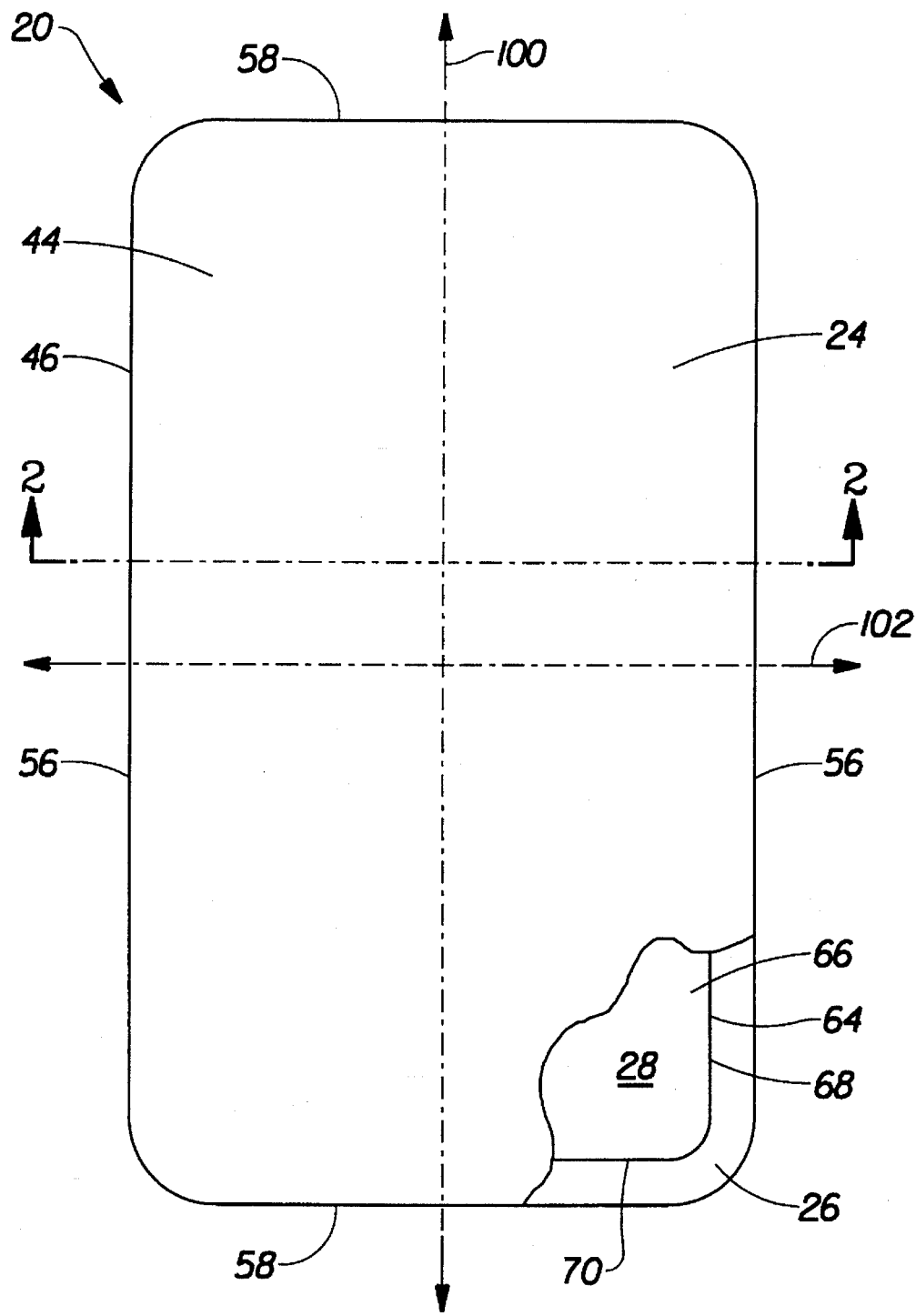
FIG. 1 is a plan view of an incontinent pad embodiment of the present invention having portions cut away to reveal underlying structure.

FIG. 1 is a plan view of the incontinent pad 20 of the present invention with portions of the structure being cutaway to more clearly show the construction of the incontinent pad 20 and with the portion of the incontinent pad which faces or contacts the wearer, the inner surface, oriented towards the viewer. As shown in FIG. 1, the incontinent pad 20 preferably comprises a liquid pervious topsheet 24; a liquid impervious backsheet 26 joined with the topsheet 24; and an absorbent core 28 positioned between the topsheet 24 and the backsheet 26.

The incontinent pad 20 also has two centerlines, a longitudinal centerline 100 and a transverse centerline 102. The term "longitudinal", as used herein, refers to a line, axis, or direction in the plane of the incontinent pad 20 that is generally aligned with (e.g. approximately parallel with) a vertical plane which bisects a standing wearer into left and right halves when the incontinent pad 20 is worn. The terms "transverse" and "lateral", as used herein, are interchangeable and refer to a line, axis or direction which lies within the plane of the incontinent pad that is generally perpendicular to the longitudinal direction.

The incontinent pad 20 is shown in FIG. 1 to have an inner surface 44 (facing the viewer in FIG. 1), an outer surface 46 opposed to the inner surface 44, and a periphery which is defined by the outer perimeter or edges of the incontinent pad 20 in which the longitudinal edges are designated 56 and the end edges are designated 58. The inner surface 44 of the incontinent pad 20 comprises that portion of the incontinent pad 20 which is positioned adjacent to the wearer's body during use (i.e., the inner surface 44 is generally formed by at least a portion of the topsheet 24 and other components joined to the topsheet 24). The outer surface 46 comprises that portion of the incontinent pad 20 which is positioned away from the wearer's body (i.e., the outer surface 46 is generally formed by at least a portion of the backsheet 26 and other components joined to the backsheet 26). As used herein, the term "joined" encompasses configurations whereby an element is directly secured to the other element by affixing the element directly to the other element, and configurations whereby the element is indirectly secured to the other element by affixing the element to intermediate member(s) which in turn are affixed to the other element.

FIG. 1 shows a preferred embodiment of the incontinent pad 20 in which the topsheet 24 and the backsheet 26 have length and width dimensions generally larger than those of the absorbent core 28. The topsheet 24 and the backsheet 26 extend beyond the edges of the absorbent core 28 to thereby form the periphery of the incontinent pad 20.

The absorbent core 28 may be any absorbent member which is generally compressible, conformable, non-irritating to the wearer's skin, and capable of absorbing and retaining liquids such as urine and other certain body exudates. As shown in FIG. 1, the absorbent core 28 has an outer surface 64, an inner surface 66, side edges 68, and end edges 70. The absorbent core 28 may be manufactured in a wide variety of sizes and shapes (e.g., rectangular, oval, hourglass, dog bone, asymmetric, etc.) and from a wide variety of liquid-absorbent materials commonly used in incontinent pads and other absorbent articles such as comminuted wood pulp which is generally referred to as airfelt. Examples of other suitable absorbent materials include creped cellulose wadding; meltblown polymers including coform; chemically stiffened, modified or cross-linked cellulosic fibers; tissue including tissue wraps and tissue laminates; absorbent foams; absorbent sponges; superabsorbent polymers; absorbent gelling materials; or any equivalent material or combinations of materials.

The configuration and construction of the absorbent core 28 may vary (e.g., the absorbent core may have varying caliper zones, a hydrophilic gradient, a superabsorbent gradient, or lower average density and lower average basis weight acquisition zones; or may comprise one or more layers or structures). However, the total absorbent capacity of the absorbent core 28 should be compatible with the design loading and the intended use of the incontinent pad 20. The size and absorbent capacity of the absorbent core 28 may also be varied to accommodate wearers ranging from infants through adults.

Exemplary absorbent structures for use as the absorbent core 28 of the present invention that have achieved wide acceptance and commercial success are described in U.S. Pat. No. 4,610,678 entitled "High-Density Absorbent Structures" issued to Weisman et al. on Sep. 9, 1986; U.S. Pat. Nos. 4,673,402 entitled "Absorbent Articles With Dual-Layered Cores" issued to Weisman et al. on Jun. 16, 1987; U.S. Pat. Nos. 4,888,231 entitled "Absorbent Core Having A Dusting Layer" issued to Angstadt on Dec. 19, 1989; and U.S. Pat. No. 4,834,735, entitled "High Density Absorbera Members Having Lower Density and Lower Basis Weight Acquisition Zones", issued to Alemany et al. on May 30, 1989. The absorbent core may further comprise the dual core system containing acquisition/distribution core of chemically stiffened fibers positioned over the absorbent storage cores as detailed in U.S. Pat. No. 5,234,423, entitled "Absorbent Article With Elastic Waist Feature and Enhanced Absorbency" issued to Alemany et al., on Aug. 10, 1993; and in U.S. Pat. No. 5,147,345, entitled "High Efficiency Absorbent Articles For Incontinence Management" issued to Young, LaVon and Taylor on Sep. 15, 1992. All of these patents are incorporated herein by reference.

The backsheet 26 is positioned adjacent the outer surface 64 of the absorbent core 28 and is preferably joined thereto by attachment means (not shown) such as those well known in the art. For example, the backsheet 26 may be secured to the absorbent core 28 by a uniform continuous layer of adhesive, a patterned layer of adhesive, or an array of separate lines, spirals, or spots of adhesive. Adhesives which have been found to be satisfactory are manufactured by H. B. Fuller Company of St. Paul, Minn. and marketed as HL-1258. An example of a suitable attachment means comprising an open pattern network of filaments of adhesive is disclosed in U.S. Pat. No. 4,573,986 entitled "Disposable Waste-Containment Garment", which issued to Minetola et al. on Mar. 4, 1986. Another suitable attachment means comprising several lines of adhesive filaments swirled into a spiral pattern is illustrated by the apparatus and methods shown in U.S. Pat. No. 3,911,173 issued to Sprague, Jr. on Oct. 7, 1975; U.S. Pat. No. 4,785,996 issued to Ziecker, et al. on Nov. 22, 1978; and U.S. Pat. No. 4,842,666 issued to Werenicz on Jun. 27, 1989. Each of these patents are incorporated herein by reference. Alternatively, the attachment means may comprise heat bonds, pressure bonds, ultrasonic bonds, dynamic mechanical bonds, or any other suitable attachment means or combinations of these attachment means as are known in the art.

The backsheet 26 is impervious to liquids (e.g., urine) and is preferably manufactured from a thin plastic film, although other flexible liquid impervious materials may also be used. As used herein, the term "flexible" refers to materials which are compliant and will readily conform to the general shape and contours of the human body. The backsheet 26 prevents the exudates absorbed and contained in the absorbent core 28 from wetting articles which contact the diaper 20 such as bedsheets and undergarments. Further, the backsheet 26 may permit vapors to escape from the absorbent core 28 (i.e., breathable) while still preventing exudates from passing through the backsheet 26. Thus, the backsheet 26 may comprise a woven or nonwoven material, polymeric films such as thermoplastic films of polyethylene or polypropylene, or composite materials such as a film-coated nonwoven material. An example of a suitable backsheet is a thermoplastic film having a thickness of from about 0.012 mm (0.5 mil) to about 0.051 mm (2.0 mils). Other suitable materials for the backsheet 26 include RR8220 blown films and RR5475 cast films as manufactured by Tredegar Industries, Inc. of Terre Haute, IN. The backsheet 26 is preferably embossed and/or matte finished to provide a more cloth like appearance.

The topsheet 24 is positioned adjacent the inner surface 66 of the absorbent core 28 and is preferably joined thereto and to the backsheet 26 by attachment means (not shown) such as those well known in the art. Suitable attachment means are described with respect to joining the backsheet 26 to the absorbent core 28. In a preferred embodiment of the present invention, the topsheet 24 and the backsheet 26 are joined directly to each other in the incontinent pad periphery and are indirectly joined together by directly joining them to the absorbent core 28 by the attachment means (not shown).

The topsheet 24 is compliant, soft feeling, and non-irritating to the wearer's skin. Further, the topsheet 24 is preferably liquid pervious permitting liquids (e.g., urine) to readily penetrate through its thickness. A suitable topsheet 24 may be manufactured from a wide range of materials, such as porous foams; reticulated foams; apertured plastic films; or woven or nonwoven webs of natural fibers (e.g., wood or cotton fibers), synthetic fibers (e.g., polyester or polypropylene fibers), or a combination of natural and synthetic fibers. The topsheet 24 is preferably made of a hydrophobic material to isolate the wearer's skin from liquids which have passed through the topsheet 24 and are contained in the absorbent core 28 (i.e. to prevent rewet). If the topsheet 24 is made of a hydrophobic material, at least the upper surface of the topsheet 24 is treated to be hydrophilic so that liquids will transfer through the topsheet more rapidly. This diminishes the likelihood that body exudates will flow off the topsheet 24 rather than being drawn through the topsheet 24 and being absorbed by the absorbent core 28. The topsheet 24 can be rendered hydrophilic by treating it with a surfactant. Suitable methods for treating the topsheet 24 with a surfactant include spraying the topsheet 24 material with the surfactant and immersing the material into the surfactant. A more detailed discussion of such a treatment and hydrophilicity is contained in U.S. Pat. No. 4,988,344 entitled "Absorbent Articles with Multiple Layer Absorbent Layers" issued to Reising, et al on Jan. 29, 1991 and U.S. Pat. No. 4,988,345 entitled "Absorbent Articles with Rapid Acquiring Absorbent Cores" issued to Reising on Jan. 29, 1991, each of which is incorporated by reference herein.

There are a number of manufacturing techniques which may be used to manufacture the topsheet 24. For example, the topsheet 24 may be a nonwoven web of fibers. When the topsheet 24 comprises a nonwoven web, the web may be spunbonded, carded, wet-laid, melt-blown, hydroentangled, combinations of the above, or the like. A suitable topsheet 24 is carded and thermally bonded by means well known to those skilled in the fabrics art. A satisfactory topsheet 24 comprises staple length polypropylene fibers having a denier of about 2.2. As used herein, the term "staple length fibers" refers to those fibers having a length of at least about 15.9 mm (0.625 inches). Preferably, the topsheet 24 has a basis weight from about 18 to about 25 grams per square meter. A suitable topsheet is manufactured by Veratec, Inc., a Division of International Paper Company, of Walpole, Mass. under the designation P-8.

In use, the incontinent pad 20 can be held in place by any support means or attachment means well-known for such purposes. Preferably, the incontinent pad 20 is placed in the user's undergarment or panty and secured thereto by a fastener such as an adhesive 30, shown in FIG. 2. The adhesive 30 provides a means for securing the incontinent pad in the crotch portion of the undergarment. Thus, a portion or all of the outer surface of the backsheet 26 may be coated with an adhesive. Any adhesive or glue used in the art for such purposes can be used for the adhesive herein, with pressure-sensitive adhesives being preferred. Suitable adhesives are Century A-305-IV manufactured by the Century Adhesives Corporation of Columbus, Ohio; and Instant Lock 34-2823 manufactured by the National Starch and Chemical Company of Bridgewater, N.J. Suitable adhesive fasteners are also described in U.S. Pat. No. 4,917,697. Before the incontinent pad is placed in use, the pressure-sensitive adhesive 30 is typically covered with a removable release liner 32 in order to keep the adhesive from drying out or adhering to a surface other than the crotch portion of the undergarment prior to use. Suitable release liners are also described in the above-referenced U.S. Pat. No. 4,917,697. Any commercially available release liners commonly used for such purposes can be utilized herein. Non-limiting examples of suitable release liners are BL30MG-A Silox E1/0 and BL30MG-A Silox 4P/O both of which are manufactured by the Akrosil Corporation of Menasha, Wis. The incontinent pad 20 of the present invention is used by removing the release liner and thereafter placing the incontinent pad in a panty or undergarment so that the adhesive contacts the panty or undergarment. The adhesive maintains incontinent pad in position within the panty or undergarment during use.

In a preferred embodiment of the present invention, an acquisition layer(s) may be positioned between the topsheet and the absorbent core. The acquisition layer may serve several functions including improving wicking of liquids over and into the absorbent core. There are several reasons why the improved wicking of liquids is important, including providing a more even distribution of the liquids throughout the absorbent core and allowing the incontinent pad 20 to be made relatively thin. (The wicking referred to herein may encompass the transportation of liquids in one, two, or all directions, i.e., in the x-y plane and/or in the z-direction.) The acquisition layer may be comprised of several different materials including nonwoven or woven webs of synthetic fibers including polyester, polypropylene, or polyethylenes; natural fibers including cotton or cellulose; blends of such fibers; or any equivalent materials or combinations of materials. In a preferred embodiment, the acquisition layer may be joined with the topsheet by any of the conventional means for joining webs together.

The backsheet 26 includes pleats 110 extending longitudinally along the length of the incontinent pad 20. The pleats 110 extend in a direction substantially parallel to the longitudinal axis 100 of the incontinent pad. The pleats 110 are tacked or secured with a liquid soluble adhesive 115. The liquid soluble adhesive 115 may be placed along the entire length of the pleat 110 or at discrete locations along the length of the pleat. Suitable liquid soluble adhesives are manufactured by H. B. Fuller Company of St. Paul, Minn. and marketed as NP-2088 and NP-2089.

The liquid soluble adhesive 115 dissolves when exposed to liquid permitting the pleats 110 to expand, open or unfold, thus allowing the backsheet 26 to expand in the transverse direction. Without the expansion of the pleats 110 in the backsheet 26, s the expansion of the absorbent core 28 would deform the shape of the incontinent pad 20 causing an increase in discomfort and a decrease in its liquid acquisition properties. The expansion of the pleats in the backsheet 26 also prevents the absorbent core 28 from being squeezed as it expands so that the danger of rewet is decreased.

Figure 2:
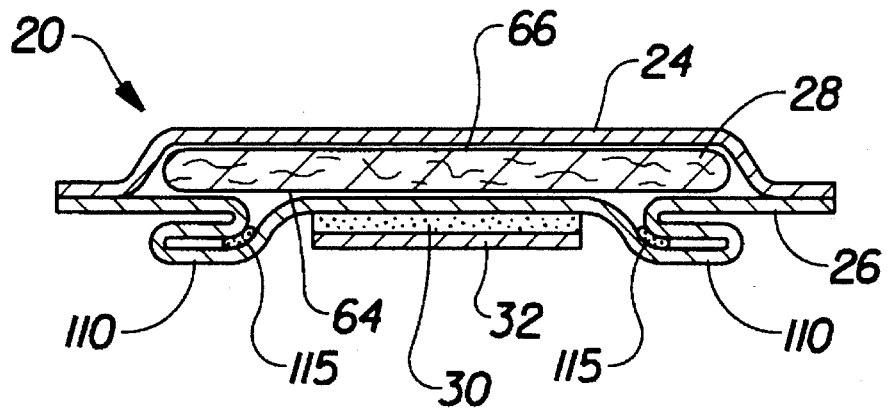
FIG. 2 is a cross-sectional view taken along section line 2—2 of FIG. 1.

In the embodiment shown in FIG. 2, the incontinent pad 20 includes a pair of pleats 110 positioned on either side of the adhesive 30. Alternatively, the incontinent pad may comprise a single pleat, or may comprise a plurality of pleats extending along the entire length or a portion of the length of the incontinent pad 20.

In another embodiment (not shown), the pleats 110 may extend in a direction substantially parallel to the transverse axis 102 of the incontinent pad 20. Thus, the pleats allow the backsheet 26 to expand in the longitudinal direction and thus allow the absorbent core to expand in the same longitudinal direction.

Figure 3:
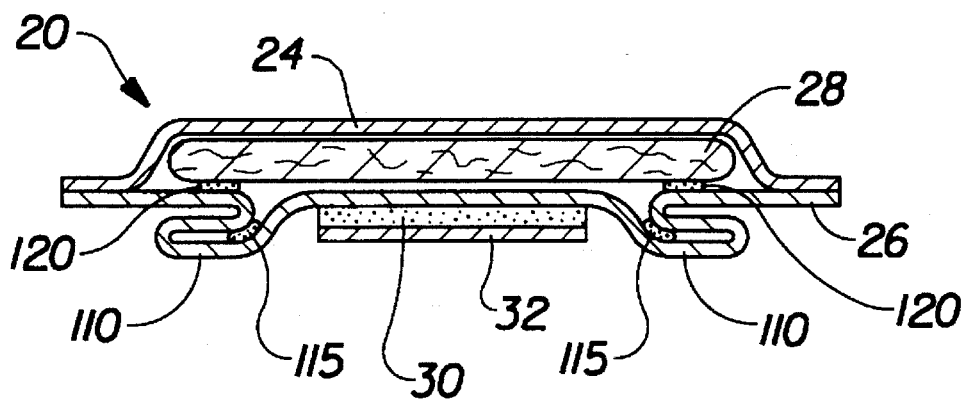
FIG. 3 is a cross-sectional view of another embodiment of an incontinent pad of the present invention.

In the embodiment shown in FIG. 3, the incontinent pad 20 includes a pair of pleats 110 extending in a direction substantially parallel to the longitudinal axis 100 of the incontinent pad. The pleats 110 are tacked with a liquid soluble adhesive 115. The pleats 110 are also tacked to the absorbent core 28 with a liquid soluble adhesive 120.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article having a longitudinal axis and a transverse axis, said absorbent article comprising: a liquid pervious topsheet, a liquid impervious backsheet joined to said topsheet, and an absorbent core positioned between said topsheet and said backsheet, said absorbent core comprising a material that expands when wetted, said backsheet having at least one pleat, said pleat being tacked with a liquid soluble adhesive such that when said liquid soluble adhesive is wetted said adhesive dissolves allowing said pleat to expand as said absorbent core expands.

2. The absorbent article of claim 1 wherein said at least one pleat extends in a direction substantially parallel to said longitudinal axis.

3. The absorbent article of claim 1 wherein said backsheet includes a plurality of pleats.

4. The absorbent article of claim 3 wherein said pleats extend in a direction substantially parallel to said longitudinal axis.

5. The absorbent article of claim 3 wherein said pleats extend in a direction substantially parallel to said transverse axis.

6. The absorbent article of claim 1 further comprising an adhesive for securing said absorbent article in a user's undergarment.

7. The absorbent article of claim 1 wherein said absorbent article is an incontinent pad.

8. The absorbent article of claim 1 wherein said absorbent core contains absorbent gelling material.

9. The absorbent article of claim 1 further comprising a liquid soluble adhesive securing said at least one pleat to said absorbent core.

* * * * *